(12) United States Patent
Powell et al.

(10) Patent No.: US 12,372,510 B2
(45) Date of Patent: Jul. 29, 2025

(54) FLUID CONDITION MONITORING SYSTEM AND APPARATUS

(71) Applicant: GLOBAL HEAT TRANSFER LIMITED, Stone (GB)

(72) Inventors: Timothy James Powell, Stafford (GB); Daniel John Wynne Ellis, Merseyside (GB); Clive Jones, Brocton (GB)

(73) Assignee: GLOBAL HEAT TRANSFER LIMITED, Staffordshire (GB)

( * ) Notice: Subject to any disclaimer, the term of this patent is extended or adjusted under 35 U.S.C. 154(b) by 259 days.

(21) Appl. No.: 17/770,808

(22) PCT Filed: Oct. 22, 2020

(86) PCT No.: PCT/GB2020/000088
§ 371 (c)(1),
(2) Date: Apr. 21, 2022

(87) PCT Pub. No.: WO2021/079080
PCT Pub. Date: Apr. 29, 2021

(65) Prior Publication Data
US 2022/0404332 A1 Dec. 22, 2022

(30) Foreign Application Priority Data
Oct. 24, 2019 (GB) ...................................... 1915411

(51) Int. Cl.
*G01N 33/28* (2006.01)
(52) U.S. Cl.
CPC ................ *G01N 33/2888* (2013.01)
(58) Field of Classification Search
CPC .................................................. G01N 33/2888
(Continued)

(56) References Cited

U.S. PATENT DOCUMENTS 4,528,842 A * 7/1985 Brown .................. E21B 47/085
73/152.49
5,156,006 A * 10/1992 Broderdorf ............. A23L 3/362
62/70

(Continued)

FOREIGN PATENT DOCUMENTS

DE 1911656 A1 9/1970

OTHER PUBLICATIONS

International Search Report and Written Opinion issued in PCT International Application No. PCT/GB2020/000088, mailed May 25, 2021, 15 pages.

*Primary Examiner* — Walter L Lindsay, Jr.
*Assistant Examiner* — Philip T Fadul
(74) *Attorney, Agent, or Firm* — Buchanan Ingersoll & Rooney PC

(57) ABSTRACT

An improved system and apparatus for testing thermal fluids in which the condition of a heat transfer fluid is measured. The system includes a sample vessel with a sample inlet for receiving a sample of heat transfer fluid from the heat transfer system and a sample outlet for returning the sample of heat transfer fluid to the heat transfer system, a heat transfer fluid condition monitor in fluid contact with the sample vessel measures one or more physical parameters of the heat transfer fluid and a control system which controls operation of the condition monitor and the sample vessel and which analyses the measured physical parameters of the heat transfer fluid. The system provides for predictive maintenance which is significantly more cost effective than preventative maintenance. It also ensures, as far as possible, that preventative maintenance can also be carried out while the system is running in normal production mode.

19 Claims, 4 Drawing Sheets

(58) Field of Classification Search
USPC .......................................................... 73/53.05
See application file for complete search history.

(56) References Cited

U.S. PATENT DOCUMENTS

| | | | | |
|---|---|---|---|---|
| 5,708,196 | A | * | 1/1998 | Tolvanen ................ G01N 25/04 |
| | | | | 73/61.76 |
| 2004/0159145 | A1 | * | 8/2004 | Seevers ............... G01N 33/2894 |
| | | | | 73/61.42 |
| 2007/0231911 | A1 | | 10/2007 | DeNatale et al. |
| 2017/0219550 | A1 | | 8/2017 | Campan |
| 2019/0257700 | A1 | * | 8/2019 | Lewis ..................... G01K 13/02 |

* cited by examiner

FLUID CONDITION MONITORING SYSTEM AND APPARATUS

CROSS REFERENCE TO RELATED APPLICATIONS

This application is a U.S. National Phase Application of PCT International Application No. PCT/GB2020/000088, filed Oct. 22, 2020, which claims benefit of priority from Great Britain Patent Application No. 1915411.1, filed Oct. 24, 2019. The contents of these applications are incorporated herein by reference.

FIELD OF INVENTION

The present invention relates to a fluid condition monitoring system and apparatus and in particular to a system and apparatus for measuring the condition of heat transfer fluid.

BACKGROUND OF THE INVENTION

A heat transfer fluid is a liquid such as a thermal oil or gas, specifically manufactured for the purpose of transmitting heat from one system to another. It may be used to prevent overheating, for heating, or for storing thermal energy. A variety of industrial manufacturing applications require heat transfer.

Heating and cooling products in a food and beverage processing plant often requires the use of a heat exchanger. Heat exchangers may contain heat transfer fluids that absorb excess heat energy and take it away from the product, or transfer heat energy to the product. Applications of heat exchangers in food and beverage processing include brewing of beer, vegetable oil deodorising, food additive manufacturing, food packaging production and food preparation including baking, frying and cooking.

Pharmaceutical processing also requires the use of food grade heat transfer fluids in case of incidental contact with the product. Food grade heat transfer fluids are colourless, odourless, non-hazardous, non-toxic and have NSF HT1 food standard accreditation.

Chemical engineers use heat transfer for indirect heating of process liquids and polymers, single fluid batch processing, pipeline tracing, energy recovery, low pressure cogeneration, drying and heating of bulk materials and gas processing. These chemical reactions often occur at high temperatures, which must be maintained for prolonged periods.

Engineers working in plastic, polymer and styrene manufacturing plants will use heat transfer systems for a range of applications such as moulding, extrusion, press heating, line tracing, coating rolls and vulcanising. These applications require heat transfer fluid with a broad temperature range to ensure maximum efficiency and effective heat transfer. Heat transfer fluid are used in other sectors including solar power, industrial laundries, asphalt plants and engineered wood applications.

All heat transfer fluids degrade over time. In the case of thermal oils, for every 10° C. increase in temperature over its recommended upper operating temperature limit, the lifespan of a heat transfer fluid may decrease by half.

Heat transfer fluids can degrade by oxidation when the fluid reacts with oxygen in the air by a free radical mechanism. The rate of oxidation increases with temperature and the reaction causes carbon to form. Thermal degradation or thermal cracking may occur if a thermal fluid is heated above the maximum film temperature specified by the manufacturer. This leads to vaporisation and the formation of carbon. Vaporisation results in increased viscosity of the fluid, which means more energy is required to pump it around the system and this leads to increased costs for businesses.

When the concentration of carbon reaches a certain level, it starts to deposit in a sludge on the insides of the pipework, in a process known as fouling. The sludge accumulates, particularly in low flow areas such as reservoirs and expansion tanks and reduces the efficiency of heat exchange. This also increases costs for businesses.

These contaminants can reduce thermal efficiency of the system, reduce the life of the thermal fluid and lead to the formation of hot spots on heater coils. These hot spots can result in coil failure and fire. Circulating debris in any system, at any stage of its lifecycle is concerning as it can erode the pipework, accelerate the oxidation of the fluid and decrease the thermal efficiency of the heat transfer fluid. Debris will also act like a grinding paste on pump seals and impellers that will eventually lead to leaks.

Manufacturers who use heat transfer fluid in their process applications are always looking to improve a range of critical factors which affect business performance including, system availability, maintenance and management costs, operational costs and regulatory compliance. When a manufacturing process application "goes down", production slows, product quality can be negatively affected, or production stops altogether. Despite a slow-down or shutdown in production, the business still must meet its financial obligations including; staff, rent, rates and utilities. Therefore, every hour where production is not at its optimum negatively affects a business's financial operating model.

Health and safety legislation requires that employers provide a safe working environment. DSEAR (Dangerous Substances and Explosive Atmospheres Regulations) also known as ATEX/CAD in Europe, sets out a mechanism for minimising the risks where flammable materials are handled which could create an explosive atmosphere.

Heat transfer fluids experience falling flash points overtime due to the effects of high temperature. The risk increases when heat transfer fluid has degenerated, and flash points, boiling points and auto ignition temperatures have reduced—the lower the flash points, the higher the risk. This increases fire risk in the event of loss of containment and therefore, heat transfer fluid is considered a dangerous substance under DSEAR regulations. The regulations apply to all closed heat transfer systems using heat transfer fluids and oils as a method of transferring heat.

DSEAR sets minimum requirements for protection of workers from fire (& explosion) risks related to dangerous substances & potentially explosive atmospheres. DSEAR complements the requirements to manage risks under the Management of Health & Safety at Work Regulations 1999.

Employers have a legal obligation not only to comply with DSEAR but to prepare and maintain documentary evidence. Thermocare 24/7 predictive heat transfer fluid condition monitoring and management system collects, presents and stores historical data relating to preventative condition management of the heat transfer fluid.

When a fluid needs to be replaced, engineers must drain, flush and clean the system. This will ensure that the new fluid works efficiently as soon as it enters the system, maximising the fluid life and system performance.

One key issue is determining if and when fluid needs to be replaced. It is known to test heat transfer fluid in a heat transfer system by sampling the fluid and sending it for analysis. These tests include a test for high TAN (total acid number)/acidity (oxidation), carbon residue, levels of internal system fouling, viscosity and particulate quantity. In addition, on-site engineers may note that the heat transfer fluid cannot maintain the required operating temperature of the process if they are frequently turning up the temperature, but the flow rates have dropped off.

The current approach is to manually take thermal fluid samples on an ad-hoc basis at predetermined time intervals, either monthly, quarterly, six monthly or annually. The results and analysis of the data form the basis of a diagnosis for the condition of the heat transfer fluid.

SUMMARY OF THE INVENTION

An aspect of the present invention is an improved system and apparatus for testing thermal fluids.

In accordance with the first aspect of the invention there is provided a system for measuring the condition of a heat transfer fluid, the system comprising:

a sample vessel with a sample inlet for receiving a sample of heat transfer fluid from the heat transfer system and a sample outlet for returning the sample of heat transfer fluid to the heat transfer system;

a heat transfer fluid condition monitor in fluid contact with the sample vessel which measures one or more physical parameters of the heat transfer fluid; and a control system which controls operation of the condition monitor and the sample vessel and which analyses the measured physical parameters of the heat transfer fluid.

Preferably, the sample inlet is at a first end of the sample vessel.

Preferably, the sample inlet has a nozzle.

Preferably, the sample inlet directs fluid onto an internal wall of the sample vessel.

Preferably, the internal wall is curved.

Preferably, the internal wall is cylindrical.

Optionally, the base of the internal wall of the vessel is flat circular.

Optionally, the base of the internal wall of the vessel is shaped to channel the heat transfer fluid towards the outlet.

Optionally, the base of the internal wall of the vessel is conical.

Preferably, the inlet creates a fluid path that goes from the inlet to the output.

Preferably, the fluid path is substantially spiral.

Preferably, the fluid cools as it circulates along the fluid path.

Preferably, the sample output is at a second end of the vessel

Preferably, the sample outlet comprises a conduit.

Preferably, the conduit is positioned to receive fluid at or near the second and end of the vessel.

Preferably, the conduit extends towards and out of the vessel at the first end.

Preferably, the conduit extends axially from at or near the second end to the first end.

Preferably, the conduit is centrally positioned in the vessel.

Preferably the sample vessel has a cylindrical inner surface.

Optionally, the base of the internal wall of the vessel is flat circular.

Optionally, the base of the internal wall of the vessel is shaped to channel the heat transfer fluid towards the outlet.

Optionally, the base of the internal wall of the vessel is conical.

Preferably, the sample vessel has a stock of thermal fluid.

Preferably, the stock of thermal fluid is cooler than the introduced fluid.

Preferably, the sample vessel mixes the stock thermal fluid with the introduced thermal fluid so as to lower the temperature of the introduced thermal fluid so as to allow measurement of its fluid properties.

Preferably, the introduced fluid is cooled to between 20 and 90° C.

Preferably the fluid condition monitor is positioned towards the second end of the vessel.

Preferably, the fluid condition monitor measures the resistivity and/or relative permittivity of the thermal fluid.

Preferably, the measurements of resistivity and/or relative permittivity of the fluid are made relative to known values for the same thermal fluid.

Optionally, the fluid condition monitor measures at least one of the following properties of the fluid, high TAN (total acid number)/acidity (oxidation), carbon residue, levels of internal system fouling, viscosity and particulate quantity.

Preferably, the analysis of the measured physical parameters comprises transmitting sensor data from the measurements of the physical parameters transmitting the sensor data to a central location for analysis.

Preferably, the fluid condition monitor converts a measurement a numerical value which is sent as a low current signal to a control box which then converts the signal into a file that is uploaded to a data storage location.

Preferably the data storage location comprises cloud-based storage.

Preferably, the heat transfer fluid data gathered from the fluid condition monitor is transmitted to the cloud using a self-contained reprogrammable data logging device, which connects to the cloud using a low-bandwidth internet connection Optionally, the data storage location is a secure server.

Preferably, the control system controls the flow of fluid into the vessel and out from the vessel.

Preferably, the heat transfer fluid data gathered from the fluid condition monitor device is transmitted to the cloud using a self-contained reprogrammable data logging device, which connects to the cloud using a low-bandwidth internet connection.

Preferably, the heat transfer fluid data gathered from the fluid condition monitor device is represented graphically on a user interface to facilitate continuous remote monitoring of the heat transfer fluid in real time.

Optionally, the heat transfer fluid data is converted into a live feed that is displayed on a web page specific to that customer.

In accordance with a second aspect of the invention there is provided an apparatus for measuring the condition of a heat transfer fluid, the system comprising:

a sample vessel with a sample inlet for receiving a sample of heat transfer fluid from the heat transfer system and a sample outlet for returning the sample of heat transfer fluid to the heat transfer system; and a heat transfer fluid condition monitor in fluid contact with the sample vessel which measures one or more physical parameters of the heat transfer fluid.

Preferably, the sample inlet is at a first end of the sample vessel.

Preferably, the sample inlet has a nozzle.

Preferably, the sample inlet directs fluid onto an internal wall of the sample vessel.

Preferably, the internal wall is curved.

Preferably, the internal wall is cylindrical.

Preferably, the sample inlet creates a fluid path that goes from the inlet to the output.

Preferably, the fluid path is substantially spiral.

Preferably, the fluid cools as it circulates along the fluid path.

Preferably, the sample outlet is at a second end of the vessel

Preferably, the sample outlet comprises a conduit.

Preferably, the conduit is positioned to receive fluid at or near the second and end of the vessel.

Preferably, the conduit extends towards and out of the vessel at the first end.

Preferably, the conduit extends axially from at or near the second end to the first end.

Preferably, the conduit is centrally positioned in the vessel.

Preferably the sample vessel has a cylindrical inner surface.

Optionally, the base of the internal wall of the vessel is flat circular.

Optionally, the base of the internal wall of the vessel is shaped to channel the heat transfer fluid towards the outlet.

Optionally, the base of the internal wall of the vessel is conical.

Preferably, the sample vessel has a stock of thermal fluid.

Preferably, the stock of thermal fluid is cooler than the introduced fluid.

Preferably, the sample vessel mixes the stock thermal fluid with the introduced thermal fluid so as to lower the temperature of the introduced thermal fluid so as to allow measurement of its fluid properties.

Preferably, the introduced Fluid is cooled to between 20 and 90° C.

Preferably the fluid condition monitor is positioned towards the second end of the vessel.

Preferably, the fluid condition monitor measures the resistivity and/or relative permittivity of the thermal fluid.

Preferably, the measurements of resistivity and/or relative permittivity of the fluid are made relative to known values for the same thermal fluid.

Optionally, the fluid condition monitor measures at least one of the following properties of the fluid, high TAN (total acid number)/acidity (oxidation), carbon residue, levels of internal system fouling, viscosity and particulate quantity.

Preferably, the analysis of the measured physical parameters comprises transmitting sensor data from the measurements of the physical parameters transmitting the sensor data to a central location for analysis.

Preferably, the fluid condition monitor converts a measurement a numerical value which is sent as a low current signal to a control box which then converts the signal into a file that is uploaded to a data storage location.

In accordance with a third aspect of the invention there is provided a sample vessel for use with a condition monitoring apparatus with a sample inlet for receiving a sample of heat transfer fluid from the heat transfer system and a sample outlet for returning the sample of heat transfer fluid to the heat transfer system.

Preferably, the sample inlet is at a first end of the sample vessel

Preferably, the sample inlet has a nozzle.

Preferably, the sample inlet directs fluid onto an internal wall of the sample vessel.

Preferably, the internal wall is curved.

Preferably, the internal wall is cylindrical.

Preferably, the sample inlet creates a fluid path that goes from the inlet to the output.

Preferably, the fluid path is substantially spiral.

Preferably, the fluid cools as it circulates along the fluid path.

Preferably, the sample vessel outlet is at a second end of the vessel

Preferably, the sample vessel outlet comprises a conduit.

Preferably, the conduit is positioned to receive fluid at or near the second and end of the vessel.

Preferably, the conduit extends towards and out of the vessel at the first end.

Preferably, the conduit extends axially from at or near the second end to the first end.

Preferably, the conduit is centrally positioned in the vessel.

Preferably the sample vessel has a cylindrical inner surface.

Optionally, the base of the internal wall of the vessel is flat circular.

Optionally, the base of the internal wall of the vessel is shaped to channel the heat transfer fluid towards the outlet.

Optionally, the base of the internal wall of the vessel is conical.

Preferably, the sample vessel has a stock of thermal fluid.

Preferably, the stock of thermal fluid is cooler than the introduced fluid.

Preferably, the sample vessel mixes the stock thermal fluid with the introduced thermal fluid so as to lower the temperature of the introduced thermal fluid so as to allow measurement of its fluid properties.

Preferably, the introduced fluid is cooled to between 20 and 90° C.

BRIEF DESCRIPTION OF THE DRAWINGS

Embodiments of the present invention will now be described, by way of example only, with reference to the drawings, in which.

DETAILED DESCRIPTION OF THE DRAWINGS

The gathering of data to monitor the condition of the thermal fluid presents some technical issues which have been overcome using an aspect of the present invention. Thermal fluid systems typically work at temperatures between 60° C. and 400° C. Hence the need for a solution that can cope with a wide range of temperatures and pressure differentials whilst allowing technical data to be gathered to provide a more up to date measure of heat transfer fluid condition.

One solution provided by an aspect of the present invention is to reduce the thermal fluid temperature to a safe value for measurement, typically 20° C.-90° C. This is achieved using the vessel to mix the hot fluid taken from the "live" heat transfer system into the vessel where it mixes with cooler fluid. The cooler fluid already in the vessel comprises some fluid from previous samples. The unit is typically installed between the feed and return lines of the thermal customer system so there is a pressure differential that allows the thermal fluid to flow into and out of the sample system. Due to the design of the internal vessel, as the heat transfer fluid cools it circulates past the sensor via convection currents while the heat transfer fluid cools to ensure the sensor does not read stagnant heat transfer fluid. The displaced heat transfer fluid is forced back into the customers circuit on the return side where the pressure is lower, so no heat transfer fluid is lost/used in the sample process.

Figure 1:
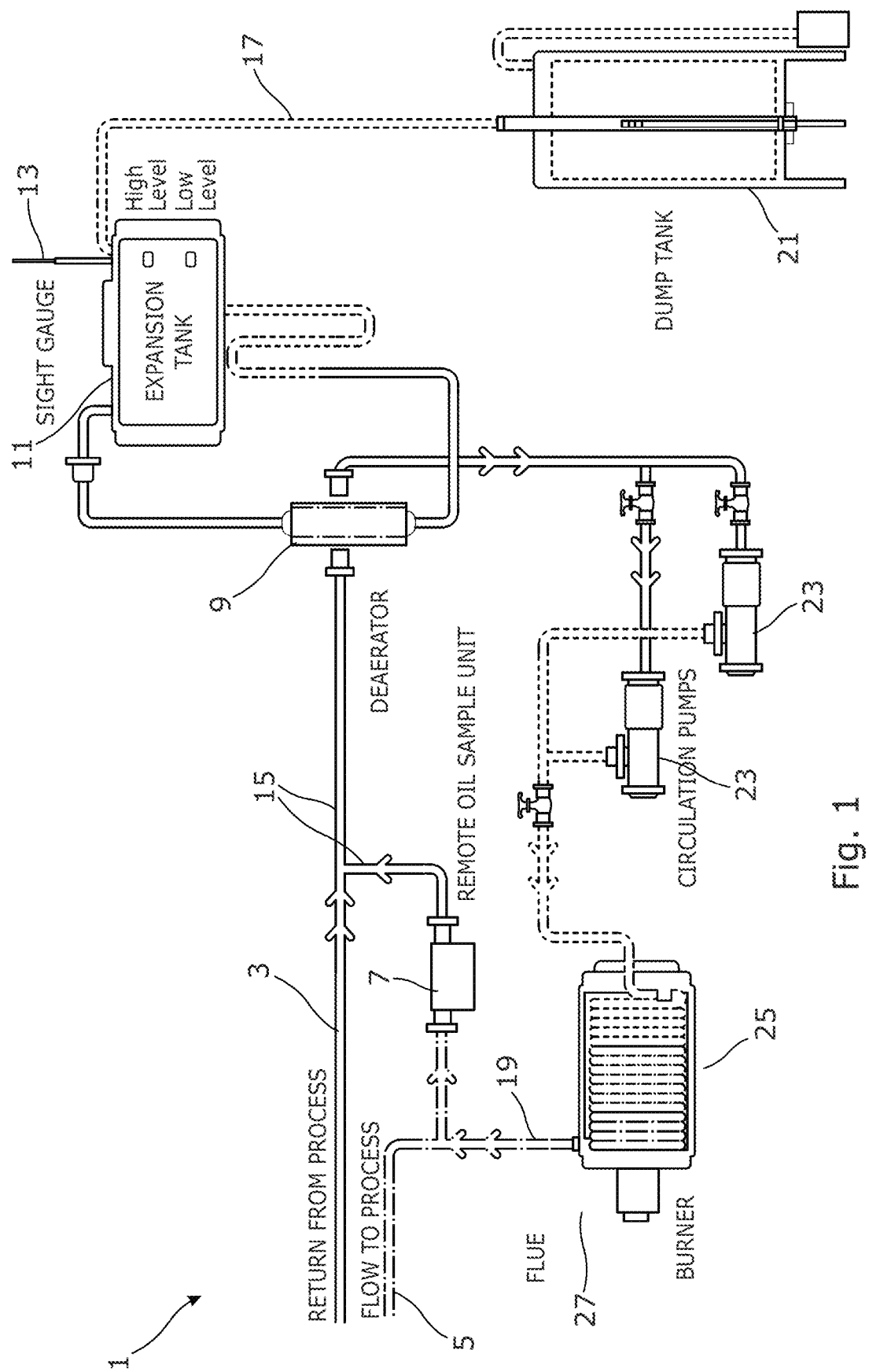
FIG. 1 is a schematic diagram of a thermal fluid system which incorporates an example of a condition monitor of an aspect of the present invention.

FIG. 1 shows an example of a typical heat transfer system. The heat transfer system 1 comprises a return path 3 from the process which is using the transfer fluid. A flow to process path 5 which takes the fluid transfer fluid to the process. Fluid sampler 7 of an aspect of the present invention is shown in more detail and FIGS. 2 and 3.

Pipes 15 receive fluid which has been subject to analysis using the fluid sampler 7 and fluid returning from the process. The fluid passes through a deaerator 9 into an expansion tank 11 which has a sight gauge 13. Pipe 17 connects the expansion tank 11 to the dump tank 21. Fluid from the expansion tank 11 and fluid from pipe 15 which has returned from the process is fed through circulation pumps 23 into a burner 25 which heats the fluid and once heated returns the fluid to the process via pipe 19. It will be appreciated that the heat transfer system shown in FIG. 1 is one example of heat transfer system.

Figure 2:
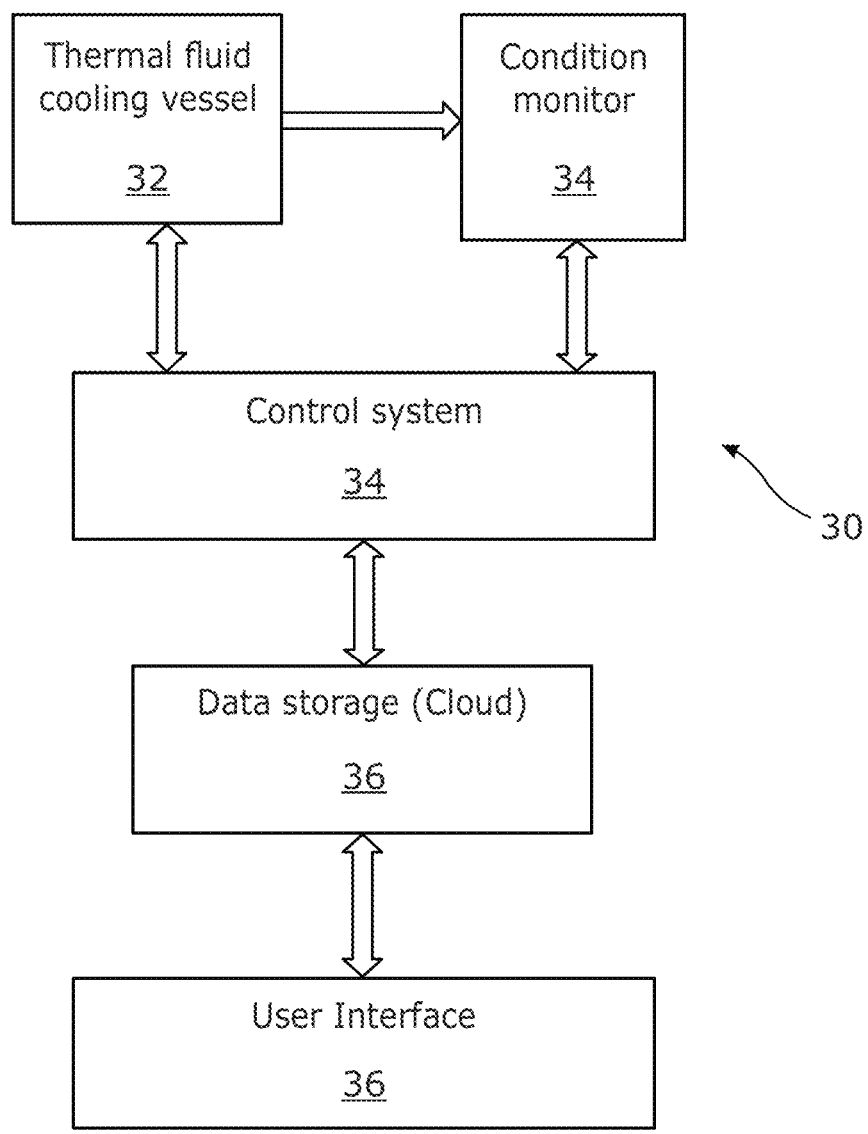
FIG. 2 is a schematic diagram of an example of a system in accordance with an aspect of the present invention.

FIG. 2 is a schematic diagram which shows an example of a system in accordance with an aspect of the present invention. The system 30 comprises a thermal fluid vessel 32 in which a sample of the thermal fluid is collected and cooled, a condition monitor which measures physical properties of the thermal fluid, a control system which controls the flow of thermal fluid into the vessel and collects data which is processed and stored 34 and then presented to a user interface 36.

Figure 3A:
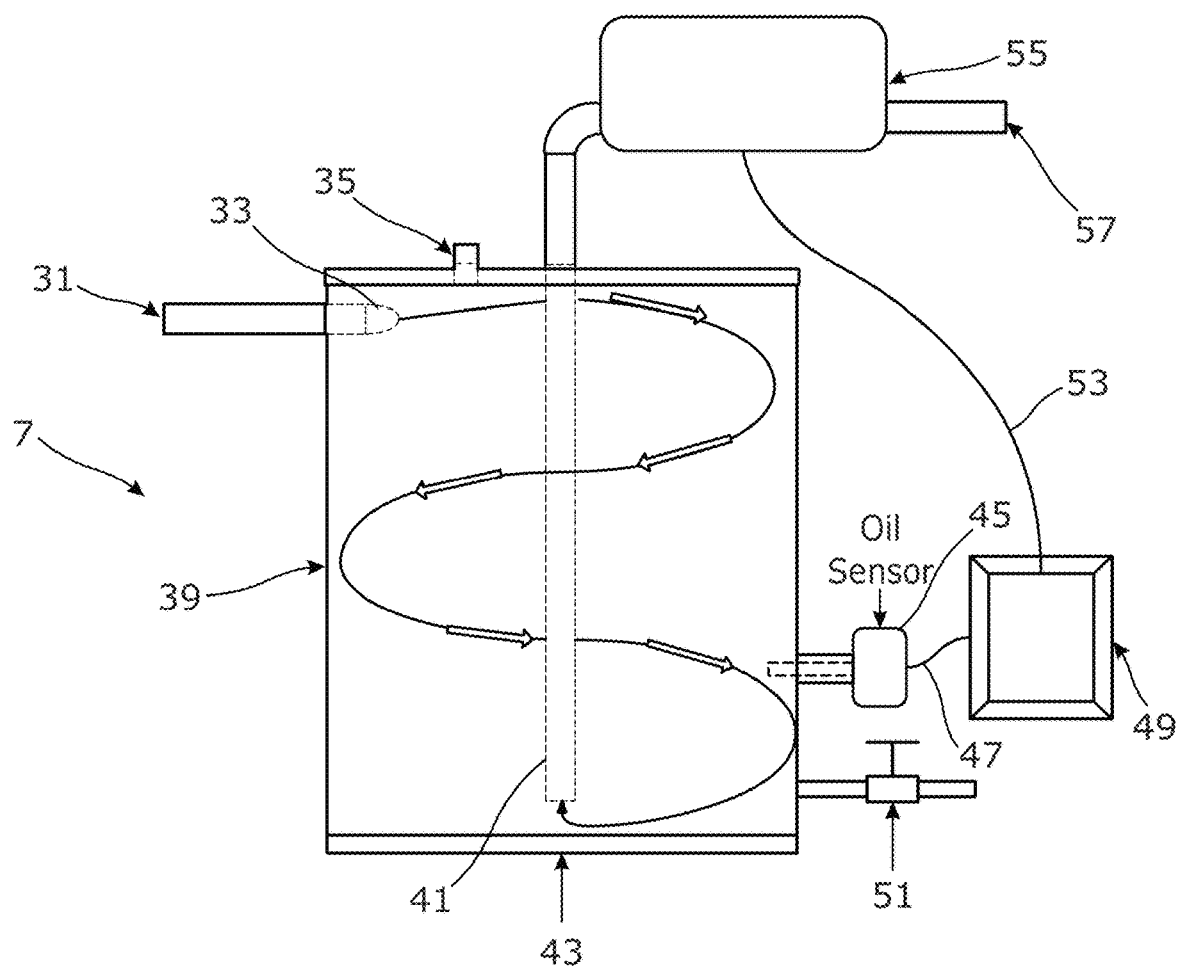
FIG. 3A is a side cross-sectional view of a condition monitoring apparatus in accordance with an aspect of the present invention and FIG. 3B is a top cross-sectional view of the same.
Figure 3B:
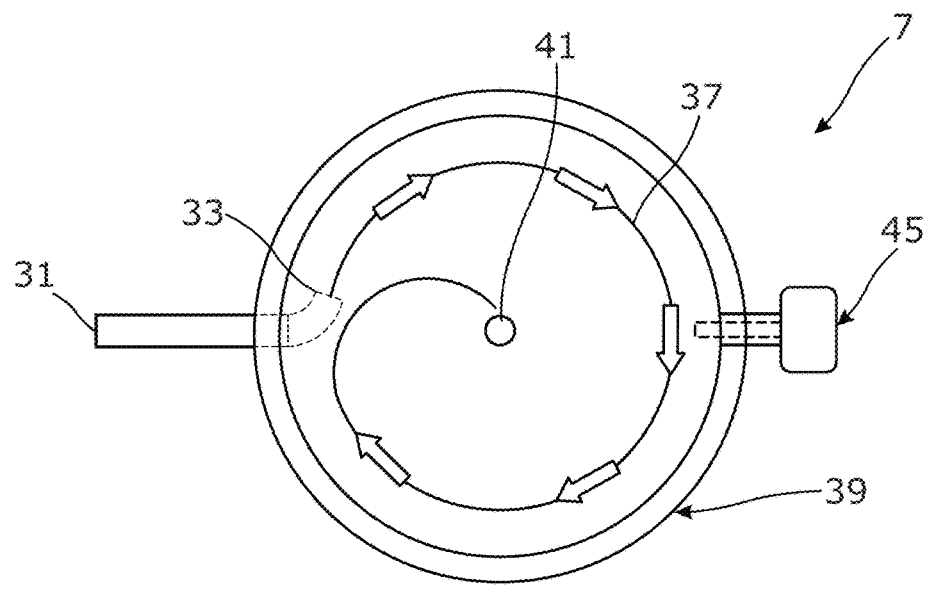

FIGS. 3A and 3B show the fluid sampler vessel 7 for use in accordance with an aspect of the present invention. The fluid sampler vessel 7 comprises a hot fluid inlet 31 which has a nozzle 33 at a first end of the vessel 7. The nozzle 33 is positioned to direct fluid towards the cylindrical side wall of the vessel such that the fluid moves along a spiral path 37 as it descends down and through the vessel to the bottom or second end of the vessel.

Towards the bottom of the fluid path 37, a sensor 45 is provide which analyses the condition of the fluid. Analysis of the fluid by sensor 45 creates data which describes the physical properties of the fluid. The sensor system is housed in a custom steel framed box with aluminium sides with two fans giving cross flow forced ventilation to assist in the cooling of the vortex mixing container. The box has two table D flanges that are connected to two high temperature flexible pipes. Different types of flanges may be used and additional isolation valves may be incorporated in the design. As there is no "standard" connection built into all thermal fluid systems the flexible pipes are made to the correct length.

The sensor data is transmitted firstly to an upload control Box 49 which then transmits the data to a central location for further analysis. In addition, the control Box 49 is operatively connected to the control valve assembly 55 which controls the flow of fluid into the vessel and out from the vessel via fluid outlet 57. Outflow is via conduit 41 (also referred to as a return line) which extends from the second end of the vessel 39 to the first end. In this embodiment, the conduit 41 is positioned centrally to extend substantially up the middle of the vessel, other locations may be used, for example, it may be offset to one side.

In use, the control valve assembly 55 receives instructions from a remote central control system via the control box 49 and the control valves of the control valve assembly 55 are opened allowing hot process fluid to enter at the top of the vessel 39. Two independent temperature sensors then shut off power to the control valves, closing them when the hot process fluid in the inlet to the sample vessel reaches a predetermined level. The fluid is directed with a right-angled bend so it is directed onto the substantially cylindrical inside wall of the vessel such that it follows a spiral pathway 39 down the wall.

Initially, the hot process fluid stays near the top of the vessel 39 as the temperature of stock thermal fluid in the container is lower and its density is higher than that of the incoming hot fluid. After a predetermined time period, the valves of the control valve assembly 55 are closed. The hot thermal fluid begins to cool from the outside of the container which causes the fluid to slowly move inside the container due to convection (the thermal fluid in the centre of the container will move to replace the fluid moving down the outside that is getting more dense as it cools. This means the sensor get a slow flow of fluid at a temperature that is within its manufacturers' tolerances.

After another predetermined amount of time the control will open the valves and another quantity of process heat transfer fluid is admitted and the displaced heat transfer fluid is sent back to the return line 41. There are two thermo switches to automatically close the valves independently of the control box if the fluid in the container gets too hot to protect the sensor and valves.

The process by which the thermal fluid is introduced into the vessel and analysed is described below in more detail with reference to FIGS. 4A to 4C. These figures show a vessel 63 and identify regions in the vessel where the thermal fluid is present at different temperatures which are labelled at the hot region 65, warm region 67 and the cool region 67. The internal pipe 71, the heat transfer fluid circulation pathway caused by convection currents 75 and the fluid pathway on injection 77 are also shown.

Figure 4A:
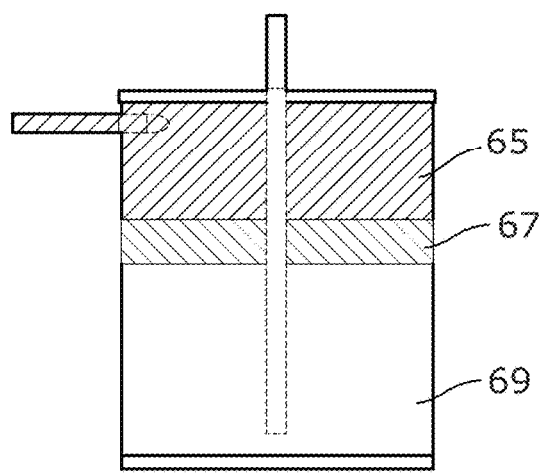
FIGS. 4A to 4C are schematic diagrams which show the flow of fluid and heat in an example of a condition monitor in accordance with an aspect of the present invention.

FIG. 4A shows the vessel 63 in static mode in which fresh hot transfer fluid has being injected and the control valves have been closed. The fluid swirls around the top of the vessel mixing with the cooler fluid evenly to keep the hot transfer fluid away from the temperature sensitive sensor and allows the maximum amount of fresh hot transfer fluid into the vessel. Thus, the hot region 65 remains at the top of the vessel, the warm region 67 in the middle and the cool region 69 at the bottom. If the transfer fluid had entered the vessel with a straight hole the fluid would spread in an uneven pattern and could make contact with the sensor damaging it.

Figure 4B:
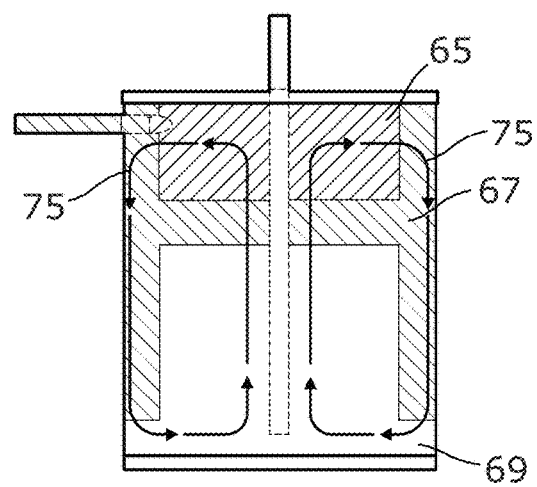

In FIG. 4B, the hot fluid is shown to have started cooling from the sides of the vessel as the heat is dissipated via thermal radiation and convection to the air. This causes movement of the fluid inside the vessel as indicated via convection currents with the cooling fluid on the sides becoming more dense and falling down the inside of the container displacing the hotter fluid forcing this up the middle to the vessel. This is shown by the change in position of the hot region 65, the warm region 67 and the cool region 69. The cooling process may take approximately 4 hours.

Figure 4C:
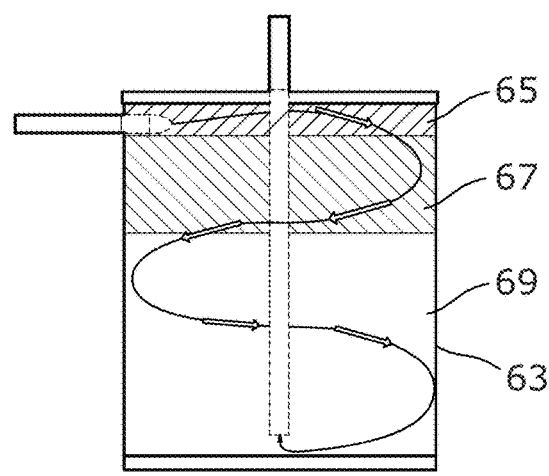

In FIG. 4C, the control valve has been opened, the duration of which is determined by the pressure differential of the process feed and return lines and is calibrated on each site) and the hot process fluid has started to fill the top of the container. It then starts to mix with the cooler fluid present. The angle of the incoming fluid causes the fluid to rotate and the displaced cool fluid flows back into the process.

In this example, the condition monitor is not "calibrated" to any specific compounds or standard chemical makeup, rather it uses a combination of measurements of resistivity and relative permittivity of the fluid. As the thermal fluid is an insulating liquid, the sensor is programmed with a set of values for each type of heat transfer fluid supplied and these are set as a baseline. As the usual chemical changes occur and the thermal fluid breaks down due to cracking, the sensor head detects this as a change of relative resistance. The electronics in the condition monitor (based on its pre-programmed values) converts the reading it has taken at the sensor head to a value, this is then is sent as 4-20 ma output that the control box then converts to a file that is uploaded to the cloud every two hours. The heat transfer fluid data gathered from the condition monitor is transmitted to the cloud using a self-contained reprogrammable data logging device, which connects to the cloud using a low-bandwidth internet connection. Sensor data recorded by the data logging device is uploaded to a cloud-based database for storage and later visualisation using commercially available viewing/interpretation products.

This allows continuous remote monitoring of the heat transfer fluid in real time. This file is then converted into a live feed that is displayed on a web page specific to that customer.

End users will be given a web link with login details for their condition monitor. A mobile software application may be used for further alerting and monitoring options. The heat transfer fluid condition data is received from the condition monitor and presented in a dashboard along with trended (historical) heat transfer fluid data. This data (in the form of graphs) is visible to both site personnel and the technical team monitoring fluid condition. If normal acceptable parameters are breached (based on the site's heat transfer fluid type, temperature range and production process) a live instant alert will be sent to site engineers and technical team, on a smart device.

A percentage scale may be used to simplify the reading to the end user as the changes will normally happen slowly over time as the heat transfer fluid breaks down over time. Algorithms within the system will also monitor the uploaded data for rapid shifts in heat transfer fluid composition and send out email alerts as well as email alerts if the heat transfer fluid hits certain thresholds in case the end user does not actively monitor the website.

In one example of the invention, the end user's website is laid out into green and red zones and the graphical chart will have options for weekly, monthly and yearly ranges so trends can be spotted. In addition, a managerial global overview website creates data that can be used to spot trends the customer or the website algorithms have missed to provide advanced warning to the client.

When the system creates an alert, the customer is contacted to understand if any system modifications have been made or there have been any known changes to the standard system operating conditions. The heat transfer fluid raw data is studied and analysed based on trended data and last known heat transfer fluid condition. Recommendations for heat transfer fluid and engineering interventions are discussed with the customer. By continuously monitoring the state of the fluid, the system assists in maintaining and extending the useable life of the heat transfer fluid, improves system performance, reduces waste and optimises product output to minimise costs.

Predictive maintenance as provided by an aspect of the present invention is significantly more cost effective than preventative maintenance as predictive maintenance takes place while the system is running in normal production mode.

An aspect of the present invention ensures, as far as possible, that preventative maintenance can also be carried out while the system is running in normal production mode. Additionally, key factors which affect heat transfer fluid condition are known in real-time and the most appropriate technical interventions are carried out without delay. Acting on heat transfer fluid condition data swiftly ensures maintenance costs are minimised and complete system shutdown is avoided whenever possible.

The cost of heating a heat transfer fluid system are significant. A manufacturer will always try to reduce the energy costs associated with the business. Keeping the heat transfer fluid in the best possible condition is essential to keep energy costs as low as possible. An aspect of the present invention ensures a production facility is operating at its optimum in order to keep operating costs as low as possible.

Improvements and modifications may be incorporated herein without deviating from the scope of the invention.

The invention claimed is:

1. A heat transfer fluid condition monitoring system, the system comprising:
    a sample vessel with a sample inlet for receiving a sample of heat transfer fluid from the heat transfer system and a sample outlet for returning the sample of heat transfer fluid to the heat transfer system;
    a heat transfer fluid condition monitor in fluid contact with the sample vessel which measures one or more physical parameters of the heat transfer fluid; and
    a control system which controls operation of the condition monitor and the sample vessel and which analyses the measured physical parameters of the heat transfer fluid,
    wherein, the sample vessel has a stock of thermal fluid, which comprises heat transfer fluid from previous samples which is cooler than the introduced sample of heat transfer fluid, and the sample of heat transfer fluid mixes with the stock thermal fluid in the sample vessel so as to lower the temperature of the sample heat transfer fluid so as to allow measurement of the fluid properties of the mixture of the stock fluid and the sample of heat transfer fluid, and wherein the inlet creates a fluid path that goes from the inlet to an output, such that the fluid path cools a fluid as it circulates along the fluid path.

2. The system as claimed in claim 1 wherein, the sample inlet is at a first end of the sample vessel.

3. The system as claimed in claim 1 wherein, the sample inlet directs fluid onto an internal wall of the sample vessel.

4. The system as claimed in claim 3 wherein, the internal wall is curved.

5. The system as claimed in claim 3 wherein, a base of the internal wall of the vessel is shaped to channel the heat transfer fluid towards the outlet.

6. The system as claimed in claim 5 wherein, the base of the internal wall of the vessel is conical.

7. The system as claimed in claim 5 wherein, the base of the internal wall of the vessel is shaped to channel the heat transfer fluid towards the outlet.

8. The system as claimed in claim 1 wherein, the fluid path is substantially spiral.

9. The system as claimed in claim 1 wherein, the output is at a second end of the vessel.

10. The system as claimed in claim 9 wherein, the sample outlet comprises a conduit which is positioned to receive fluid at or near the second end of the vessel.

11. The system as claimed in claim 10 wherein, the conduit extends towards and out of the vessel at the first end.

12. The system as claimed in claim 10 wherein, the conduit extends axially from at or near the second end to the first end.

13. The system as claimed in claim 1 wherein, the fluid condition monitor is positioned towards a second end of the vessel, and wherein the fluid condition monitor measures a resistivity and/or a relative permittivity of the thermal fluid.

14. The system as claimed in claim 1 wherein, the fluid condition monitor measures at least one of the following properties of the fluid, high TAN (total acid number)/acidity (oxidation), carbon residue, levels of internal system fouling, viscosity and particulate quantity.

15. The system as claimed in claim 1 wherein, the control system analyses the measured physical parameters by transmitting sensor data from the measurements of the physical parameters transmitting the sensor data to a central location for analysis.

16. The system as claimed in claim 1 wherein, the fluid condition monitor converts a measurement in the form of a numerical value which is sent as a low current signal to a control box which then converts the signal into a file that is uploaded to a data storage location.

17. The system as claimed in claim 1 wherein, heat transfer fluid data gathered from the fluid condition monitor is transmitted to the cloud using a self-contained reprogrammable data logging device, which connects to the cloud using a low-bandwidth internet connection.

18. The system as claimed in claim 17 wherein, the heat transfer fluid data gathered from the fluid condition monitor device is represented graphically on a user interface to facilitate continuous remote monitoring of the heat transfer fluid in real time.

19. The system as claimed in claim 17 wherein, the heat transfer fluid data is converted into a live feed that is displayed on a web page specific to a customer.

* * * * *